US00PP13111P2

(12) United States Plant Patent
Olesen et al.

(10) Patent No.: US PP13,111 P2
(45) Date of Patent: Oct. 22, 2002

(54) MINIATURE ROSE PLANT NAMED 'POULROSIT'

(76) Inventors: L. Pernille Olesen, Hillerødvejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 23 days.

(21) Appl. No.: 09/655,237

(22) Filed: Sep. 5, 2000

(51) Int. Cl.[7] ..... A01H 5/00
(52) U.S. Cl. ..... Plt./116
(58) Field of Search ..... Plt./118, 116, 125

(56) References Cited

U.S. PATENT DOCUMENTS

PP9,716 P * 12/1996 Olesen et al. ..... Plt./118
PP11,543 P * 10/2000 Olesen et al. ..... Plt./122

OTHER PUBLICATIONS

Community Plant Variety Office. "Certificate on the Grant of Community Plant Variety Rights" Jun. 19, 2000. 6 pages. EU.
UPOV–ROM, Mar. 2001, Plant Variety Database, GTI Jouve Retrieval Software, 2 citations for 'POULrosit'.*
Cooper, "Biotechnology and the Law", Section 8.05, (1998 Clark, Boardman, Callaghan), pp. 8–15 to 8–16.*

* cited by examiner

*Primary Examiner*—Howard J. Locker

(57) ABSTRACT

A new miniature rose plant which has abundant flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

The present discovery constitutes a new and distinct variety of a miniature rose plant which was discovered in a cultivated area in Fredensborg, Denmark. The mutation resulted from 'POULgold', a non-patented, miniature pot rose hybridized by the same inventors, with PBR Registration Number in Denmark, No. 2108, granted on Jan. 29, 1991. The new rose variety resulted from a naturally occurring mutation of unknown causation on a branch of 'POULgold'.

The rose plant of the present discovery has a unique combination of characteristics which are outstanding in the new variety and which distinguish it from the original rose 'POULgold' as well as all other varieties which we are aware of. For example, the new variety has:

1. Abundant, yellow colored flowers with red intonations on the margins;
2. Vigorous and compact growth,
3. Year-round flowering under glasshouse conditions;
4. Suitability for production from softwood cuttings in pots;
5. Durable flowers and foliage which make the variety suitable for distribution in the floral industry.

The combination of qualities of this variety represents significant improvement over previously available commercial cultivars of this type and distinguishes 'POULrosit' from all other varieties of which we are aware. As part of their rose development program, L. Pernille Olesen and Mogens N. Olesen budded cuttings taken from the aforementioned mutation and conducted evaluations on the resulting seedlings in a controlled environment in Fredensborg, Denmark.

Asexual reproduction of 'POULrosit' by cuttings and traditional budding onto *Rosa Multiflora* understock was first done by L. Pernille and Mogens N. Olesen in October of 1998 at their nursery in Fredensborg, Denmark. This initial and other subsequent propagations conducted in controlled environments have demonstrated that the characteristics of 'POULrosit' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULrosit'. Specifically illustrated in SHEET 1:

1. Flowering stem showing branching and the attachment of leaves, buds, and peduncles;
2. Flower bud, partially opened bud, and open bloom;
3. Flower petals, detached;
4. Sepals, receptacle, and pedicel;
5. A bare stem with some foliage as well as a bare stem exhibiting thorns;
6. Leaves.

DETAILED DESCRIPTION OF THE VARIETY

The following is a description of 'POULrosit', as observed in its growth in glasshouses in Half Moon Bay, Calif. Color references are made using The Royal Horticultural Society (London, England) Colour Chart, 1995, except where common terms of color are used.

For a comparison, several physical characteristics of the rose variety 'POULsun', a miniature rose variety from the same inventors described and illustrated in U.S. Plant Pat. No. 9,716 dated Dec. 3, 1996, are compared to 'POULrosit' in Chart 1.

CHART 1

| | 'POULrosit' | 'POULsun' |
|---|---|---|
| Petal Color, Upper Surface: | Yellow Group 4A–D with marginal intonations of Red Group 52A. | Yellow Group 13A |
| Petal Color, Reverse Surface: | Yellow Group 4A–C. | Yellow Group 13B |
| Petalage: | Double; 23 to 25 petals. | 30 to 35 |

Parent: Mutation of POULgold.
Classification:
*Botanical.*—*Rosa hybrida.*
*Commercial.*—Miniature.

FLOWER AND FLOWER BUD

Blooming habit: Continuous.
Flower bud:
*Size.*—Upon opening, 15 mm–17 mm in length from base of receptacle to end of bud.
*Bud form.*—Short, globular.
*Bud color.*—As sepals unfold Red Group 45B with intonations of Yellow Group 12B, Red Group 45B with intonations of Yellow Group 12B at ¼ opening.
*Sepals.*—Green Group 139A. Strong foliaceous appendages on three of the five sepals. Surfaces of sepals slightly pubescent. Stipitate glands are present on edges of sepals.
*Receptacle.*—Surface: Smooth. Shape: Cup-shaped. Size: 4 mm (h)×6 mm (w). Color: Yellow-Green Group 144A.
*Peduncle.*—Surface: Smooth. Length: 25 mm to 30 mm average length. Color: Yellow-Green Group 144A. Strength: Upright.
*Borne.*—Generally with one to three buds per flowering stem.
Flower bloom:
*Fragrance.*—None.
*Duration.*—As a pot plant, flowers last from 7 to 10 days. As a cut flower 4 to 5 days. Petals fall cleanly away from plant.
*Size.*—Small for a plant grown in a 12.5 cm container, which is typical in production of the variety. Average flower diameter is 35–40 mm when open.
*Form.*—Shape of flower when viewed from the side: Upon opening, upper part: Convex. Upon opening, lower part: Flat. Open flower, upper part: Flattened convex. Open flower, lower part: Flattened convex.
*Petalage.*—Average range: 23 to 25 petals under normal conditions, with 2 to 3 petaloids.
Color:
*Upon opening, petals.*—Outermost petals: Upper Surface: Yellow Group 5A. On plants grown under high light conditions margins may exhibit intonations of Red Group 44A. Reverse Side: Yellow Group 5A. On plants grown under high light conditions margins may exhibit intonations of Orange-Red Group 33A. Innermost petals: Upper Surface: Yellow Group 5A. On plants grown under high light conditions margins may exhibit intonations of Red Group 44A. Reverse Side: Yellow Group 5A. On plants grown under high light conditions margins may exhibit intonations of Orange-Red Group 33A.
*Upon opening, basal petal spots.*—None observed.
*After opening, petals.*—Outermost petals: Upper Surface: Yellow Group 4A–D, with occasional intonations of Red Group 52A. Reverse Side: Yellow Group 4A–C. Innermost petals: Upper Surface: Yellow Group 4A–D. Reverse Side: Yellow Group 4A–D.
*After opening, basal petal spots.*—None observed.
General tonality: On open flower, Yellow Group 4A and 4D. On plants grown under high light conditions, petal margins with intonations of Red Group 52A. No change in the general tonality at the end of the 7th day. Afterwards, general tonality is Yellow-Orange Group 18C.
Petals:
*Petal reflex.*—Slight.
*Petal edge.*—Uniform towards center; guard petals are retuse.
*Shape.*—Deltoid.
*Petaloids.*—2 to 3 per bloom.
*Texture.*—Thick.
*Arrangement.*—Imbricated.
Reproductive organs:
*Pollen.*—Color: Yellow-Orange Group 21A. Abundance: Average.
*Anthers.*—Size: Small. Color: Greyed-Orange Group 177A. Abundance: Very abundant.
*Filaments.*—Color: Yellow Group 2B.
*Stigmas.*—Slightly inferior relative to anthers. Color: Yellow-Green Group 145D.
*Styles.*—Color: Yellow Green Group 145C.

PLANT

Plant growth: Vigorous, upright to bushy. When grown as a 12.5 cm pot plant, the average height of the plant itself is to 25 cm and the average width is to 20 cm.
Stems:
*Color.*—Young wood: Yellow-Green Group 144A. Older wood: Yellow-Green Group 144A.
*Prickles.*—Incidence: Few. Size: Average length: 5 mm. Color: Greyed-Yellow Group 160C. Shape: Linear.
*Surface.*—Young wood: Smooth. Older wood: Smooth.
Plant foliage: Normal number of leaflets on leaves in middle of the stem: 5 leaflets.
*Leaf size.*—30 mm (l)×17 mm (w).
*Abundance.*—Average.
*Color.*—Upper Leaf Surface: Green Group 139A. Lower Leaf Surface: Green Group 138B. Juvenile foliage: Green Group 138A. Anthocyanin intonation: Occasional. Location: When present, outermost margin of juvenile leaflets. Color: Greyed-Purple Group 184B.
Plant leaves and leaflets:
*Stipules.*—Size: 4 mm–6 mm. Color: Yellow-Green Group 144A at base; Green Group 139A at tips. Stipitate glands: Present on edges of stipule.
*Petiole.*—Length: 10 mm–20 mm. Color: Yellow-Green Group 146A. Underneath: Yellow-Green Group 144A. Margins: Few to no stipitate glands present on margins.
*Rachis.*—Color: Yellow-Green Group 146A. Underneath: Yellow-Green Group 144A; sparse stipitate glands present.
*Leaflet.*—Edge: Serrated. Shape: Ovate. Texture: Thin and moderately glossy.

Disease resistance: Average resistance to mildew, black spot, and Botrytis under normal growing conditions in Half Moon Bay, Calif.

Cold hardiness: 'POULrosit' has been found to be resistant to damage from cold, heat and drought damage in USDA Zone 7.

We claim:

1. A new and distinct variety of rose plant of the miniature class, substantially as herein illustrated and described as a distinct and novel rose variety due to its abundant, yellow flowers with red intonations on petal margins, vigorous and compact growth, year round flowering under glasshouse conditions, suitability for production from softwood cuttings in pots, and durable flowers and foliage which make the variety suitable for distribution in the floral industry.

* * * * *

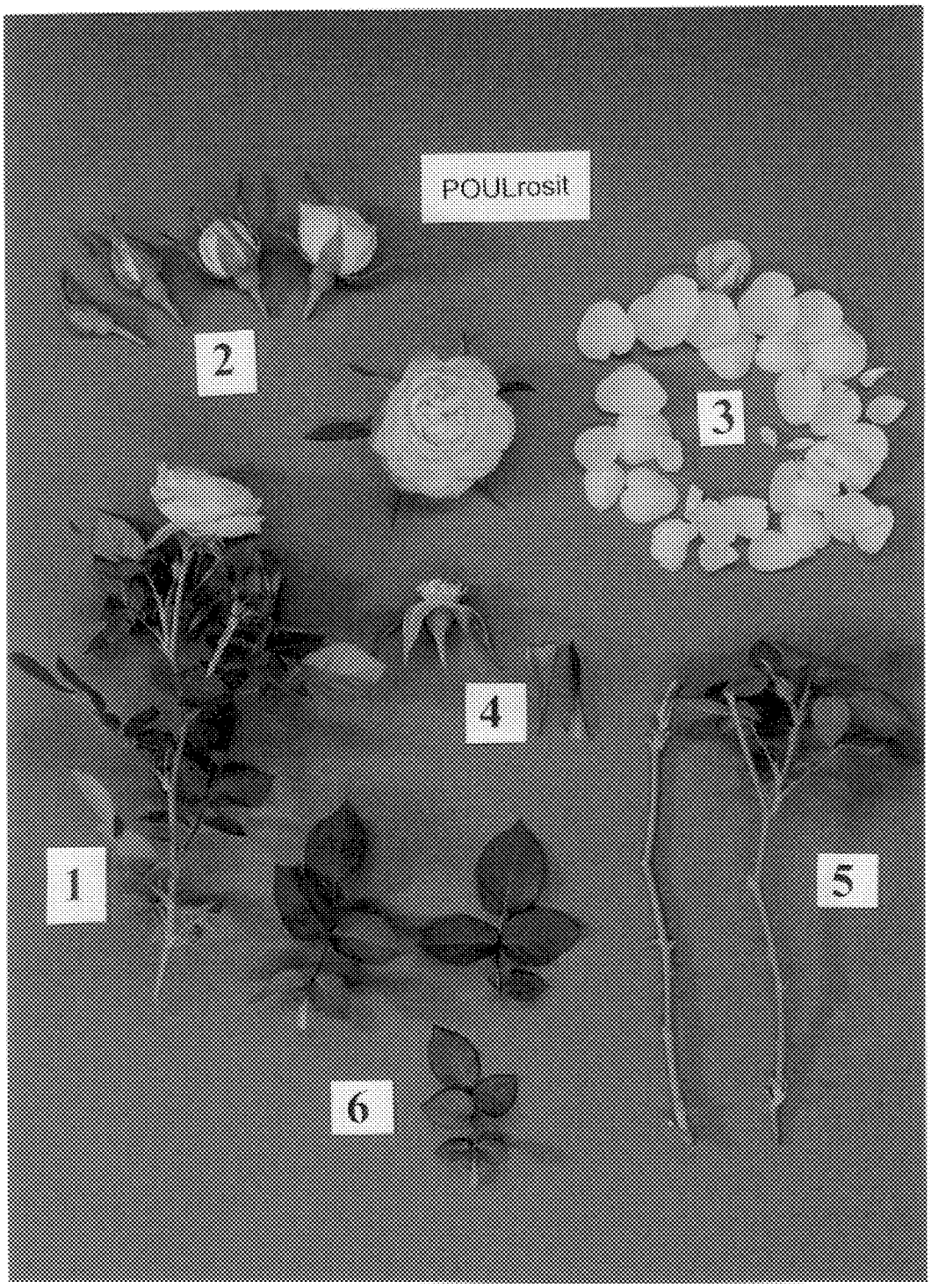
POULrosit
2
3
4
1
5
6